United States Patent
Woolford

(10) Patent No.: US 10,692,044 B2
(45) Date of Patent: Jun. 23, 2020

(54) CONSOLIDATED HEALTHCARE AND RESOURCE MANAGEMENT SYSTEM

(71) Applicant: Parallax Enterprises, LLC, Sykesville, MD (US)

(72) Inventor: Jeffrey Scott Woolford, Sykesville, MD (US)

(73) Assignee: Parallax Enterprises, LLC, Skyesville, MD (US)

( * ) Notice: Subject to any disclaimer, the term of this patent is extended or adjusted under 35 U.S.C. 154(b) by 0 days.

(21) Appl. No.: 16/128,846

(22) Filed: Sep. 12, 2018

(65) Prior Publication Data

US 2019/0138991 A1 May 9, 2019

Related U.S. Application Data

(63) Continuation of application No. 14/327,956, filed on Jul. 10, 2014, now abandoned, which is a
(Continued)

(51) Int. Cl.

| | |
|---|---|
| G06Q 10/10 | (2012.01) |
| G06Q 10/06 | (2012.01) |
| G16H 40/63 | (2018.01) |
| G06Q 50/22 | (2018.01) |
| G06F 19/00 | (2018.01) |
| A61B 34/00 | (2016.01) |

(52) U.S. Cl.
CPC ........... *G06Q 10/10* (2013.01); *G06F 19/321* (2013.01); *G06Q 10/06* (2013.01); *G06Q 50/22* (2013.01); *G16H 40/63* (2018.01); *A61B 34/25* (2016.02); *A61B 2034/252* (2016.02); *A61B 2034/256* (2016.02)

(58) Field of Classification Search
CPC ......... A61B 34/25; A61B 90/37; A61B 90/90; G06Q 10/10; G06Q 50/22; G06Q 50/24; G06F 3/017; G06F 3/011; G06F 19/00; G06F 1/14; G16H 40/63; G16H 40/20; G16H 50/30; G16H 40/67; G16H 20/40; G16H 40/40; G16H 70/20
See application file for complete search history.

(56) References Cited

U.S. PATENT DOCUMENTS

| | | | |
|---|---|---|---|
| 2004/0150678 A1* | 8/2004 | Jeong | G09G 5/003 715/867 |
| 2004/0193413 A1* | 9/2004 | Wilson | G06F 3/017 704/243 |

(Continued)

*Primary Examiner* — Joseph D Burgess
(74) *Attorney, Agent, or Firm* — Whiteford, Taylor & Preston, LLP; Peter J. Davis

(57) ABSTRACT

A technical procedure and information enhancement system comprising a multi-function colored display; a computing device having memory and processors; a touch-free gesture-responsive computer input device; computer-readable media containing computer instructions for displaying a plurality of electronic pages selected from the group consisting of a pre-procedural page, a procedure preparation page, an intra-procedural page and a post-procedural page; connection to the internet; a backup memory; a microphone; one or more video cameras situated to record the medical procedure, speakers, and an electronic signature pad.

2 Claims, 4 Drawing Sheets

Related U.S. Application Data continuation of application No. 13/526,156, filed on Jun. 18, 2012, now Pat. No. 8,930,214.

(60) Provisional application No. 61/498,472, filed on Jun. 17, 2011.

(56) References Cited

U.S. PATENT DOCUMENTS

| | | | | |
|---|---|---|---|---|
| 2005/0075544 | A1* | 4/2005 | Shapiro | G06Q 10/10 600/300 |
| 2007/0185733 | A1* | 8/2007 | Roady | G06Q 10/10 705/2 |
| 2007/0282195 | A1* | 12/2007 | Masini | A61B 90/36 600/424 |
| 2009/0016580 | A1* | 1/2009 | Yamamichi | A61B 6/502 382/128 |
| 2009/0299924 | A1* | 12/2009 | Bauer | G06F 19/3481 706/12 |
| 2010/0203937 | A1* | 8/2010 | Kondo | A63F 13/10 463/4 |

* cited by examiner

CONSOLIDATED HEALTHCARE AND RESOURCE MANAGEMENT SYSTEM

BACKGROUND OF THE INVENTION

This invention relates to methods and systems for improving the consistency, reliability, efficiency and safety of advanced complex technical procedures. In particular, this invention relates to a method and system for collecting, and storing information from various sources and inputs relating to a medical or other complex technical procedure, and making that information available to a technical procedure team in a single integrated and interactive user interface.

BRIEF SUMMARY OF THE INVENTION

In the operating room, the chief surgeon is the field marshall, the CEO, the master of ceremonies, the maestro, orchestrating complex, lengthy, and nested sets of procedures performed by various teams and sub-teams. Each member of the team has a specific set of distinct responsibilities, is responsible for committing his or her responsibilities to memory and carrying them out flawlessly. In addition to being solely responsible for knowing and executing the most critical parts of the procedure, the chief surgeon is responsible for knowing all of the procedures and parameters for which each individual member of the team is immediately responsible, and the chief surgeon has ultimate responsibility for making sure that everything happens according to plan. However, notwithstanding the number of people involved in a complex medical procedure, the chief surgeon is often the only person that knows the entire procedure and the complex interaction between the various sub-procedures. Additionally, the modern operating room often has dozens of monitors and life-sustaining devices that need to be monitored constantly, and the collective impact of their various readings understood. While numerous people are involved in monitoring various machine readings and other critical data, it is again the chief surgeon who is responsible for understanding and reacting to changes in the readings, and instructing the team accordingly. Moreover, due to the rigid hierarchical structure of most surgical teams, less senior members of the team are reluctant to make important observations outside of their own area of responsibility, and are especially reluctant to call into question steps or decisions made by the chief surgeon. When the system works as designed, it is a smooth and perfectly synchronized symphony of coordinated movements and decisions. When there is a mistake, a mis-performed or misremembered step, it can result in profound patient injury or even death.

While it goes contrary to the accepted paradigm of today's operating theater, what is needed is a system and method according to which all of the information relevant to a medical procedure are collected and presented, in the operating theater, in a user-friendly, integrated and interactive interface available to each member of the team, and in which each member of the team is trained to participate in the decision-making process based on data, procedures, and crisis management protocols presented on the interface.

The present invention is a revolutionary, patient-centered information enhancement system offering healthcare providers a real-time, interactive interface. The present invention ensures procedural accuracy with increased efficiency, resulting in significant and quantifiable patient safety advancements. Once the cultural and procedural adaptations demanded of the present invention are embraced by the medical profession, the true potential of modern healthcare will at last be realized to the benefit of both physician and patient. The results will reduce the number of avoidable iatrogenic injuries and save lives.

According to a preferred embodiment of the invention, the system of the invention includes one or more data modules containing patient information, medical records, medical procedures, and other information relevant to patient treatment and medical institution administration, a management or control module including software configured to permit and oversee data and information entry, retrieval, and display in various modes of the invention (including pre-procedure, intra-procedure, and post-procedure modes of operation), a primary display device, a sterile display assembly, a gesture-sensitive input device, various video cameras and microphones, and interfaces with operating room monitors and other medical devices. The primary display device, the sterile display assembly, the gesture-sensitive input device, the video cameras and microphones and the operating room device interfaces are primarily used during a medical procedure (the intra-procedure mode). All connections between the various physical devices of the invention may be optionally hard-wired, wireless, or combination thereof. In either case, communications between devices may be over secure local area networks, over wide area networks, or combinations thereof, using secure communication protocols.

During the pre-procedure and post-procedure modes of the invention, users may interact with the data modules and with the management and control module using standard computing devices, including desktop computers, laptop computers, notebook computers, smartphones and other mobile computing devices. The management module is optionally configured to provide different interfaces for different categories of user, depending on the mode in use. In the pre-operative mode, for example, a hospital administrator may be presented with an administrator interface; a patient may be presented with a patient interface; a surgeon may be presented with a physician's interface; nurses and other operating room personnel may be presented with yet another interface. Each of these interfaces may be configured to allow the user to interact with the management module to provide or receive general information, including information concerning the hospital, to its staff, or general medical information; additionally, the interfaces may be additionally configured to allow the user to provide or retrieve information relevant to a particular patient, to a particular procedure, or to a particular surgeon.

In the intra-procedure mode, the primary interface is the physician interface, in which the management module is configured to present various patient, procedure, and emergency information to the procedure team in an organized and easily understood fashion on the primary display device, as well as on the sterile display. During the intra-procedure mode, the management module is configured to optionally receive instructions via voice commands and/or via the gesture-sensitive input device. The management module may be also be configured to control audio and video recording of the procedure, as well as to interface with various medical devices in the room and provide redundant displays of their output on the primary display device as well as optionally on the sterile display.

Modern healthcare delivery includes both out-patient and in-patient care, depending on the complexity of the procedure required. The present invention is a scalable system which can easily be customized to accommodate a wide range of procedures, from endotracheal tube placement in an Intensive Care Unit (ICU) to cardiac stent placement in a Cardiac Catheterization Laboratory (CCL).

Additionally, while this invention was originally conceived for use in the medical profession in connection with medical procedures, the description and examples herein should not be construed to limit the invention solely to use with medical procedures. The features and principles of the invention can be adapted for and used in connection with other technical procedures, including dental orthodontic procedures and veterinary procedures. Indeed, the present invention may be used to improve resource management, operational consistency, efficiency, accuracy and safety for any technical procedure that is primarily carried out by human operators operating in a team environment; interacting with technology and tools that require high level of experience and expertise, and where performance and safety are critical to successful outcomes.

The system of the present invention communicates with various external systems through both propriety protocols and a variety of established Electronic Medical Record (EMR) standards. The software architecture allows for an adaptable communication scheme based on the desired method.

A more detailed description of features of the invention is set forth below in the detailed description of the invention, with reference to the figures. The following detailed description of the invention is not intended to limit or exclude these embodiments from the invention.

DETAILED DESCRIPTION OF THE INVENTION

Figure 1:
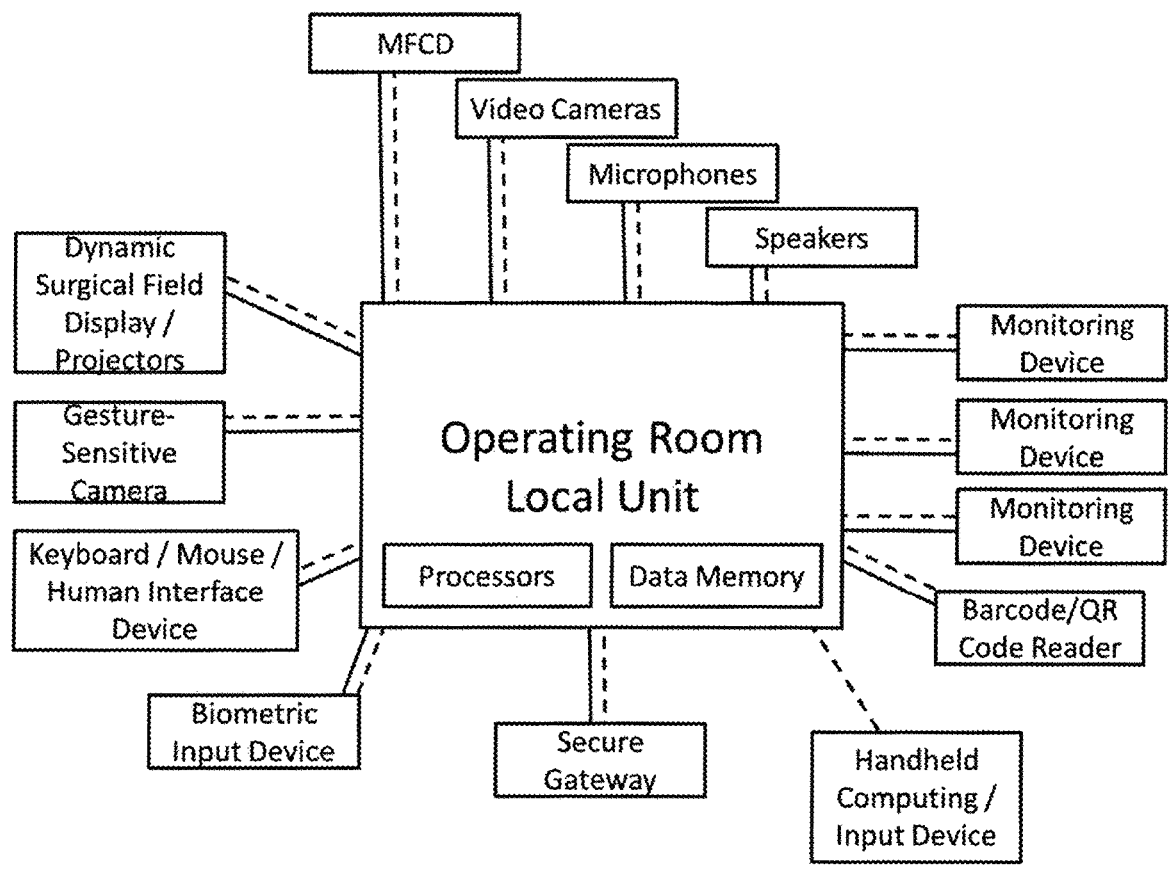
FIG. 1 is a representation of a local unit, shown being used in an operating room, and its connection to various elements of the invention according to a preferred embodiment of the invention.

Referring to FIG. 1, the invention may include a large screen multi-function display, dynamic surgical field display, gesture sensitive motion sensor, video camera, microphone, speakers, biometric input devices, barcode reader, all connected to a local data storage, processing and control unit (hereinafter the "local unit"). The local unit may also receive inputs from various monitors and medical devices, and all connections may be hardwired (as shown by the solid lines in FIG. 1) or wireless (as represented by the dashed lines in FIG. 1). The large screen multi-function color display (MFCD) situated in a prominent location in the operating theatre. The display must be large enough and situated to provide an easy to read, non-glare, crisp image of suitable size to be seen from any work station in the operative suite. In addition to the primary display screen, the system of the invention has redundant display capability, which enables various repeating display devices to be placed throughout the operating room or in an adjacent space that enables improved visibility when the MFCD is blocked.

Another primary and visible feature of the invention is a dynamic surgical field display and projection unit. This feature allows for a projector to display the redundant screen image on the sterile side of the partition sterile-dressing, frequently placed between the anesthesiologist's non-sterile working field at the patient's head and the surgeon's sterile operative field elsewhere on the patient's torso. This partition sterile dressing is colloquially and commonly referred to as the "blood-brain barrier". The dynamic surgical field display and projection unit includes a camera to view the projection field in order to determine where the screen image should be projected. The image projector and a proprietary, sterile barrier imprinted with a series of calibration marks, allow positioning for display offset and aspect reference for focal length.

The present invention may also include a gesture-sensitive camera sensor input device. This device enables control and manipulation of intraoperative page functions displayed on the MFCD via hand gestures and motions, enhancing surgical efficiency. Often, operative procedures are delayed while members of the team gather required information for the surgeon. This delay is easily mitigated by providing the surgeon with an autonomous, timely and sterile means to retrieve and display the desired information. This feature allows the surgeon to navigate to different pages stored on the system to retrieve and display information that is not on the primary display page/screen. Such additional information might include previously loaded data including laboratory results, plain films, computed tomography, etc. Additional, such additional information might include real-time intraoperative images taken during the procedure such as C-arm imaging, scope imaging, etc. This capability provides the surgeon with access to timely data via one centralized location, further increasing efficiency and reducing the time the patient is under anesthesia.

According to a preferred embodiment of the invention, the system is provided with access to a local area or wide area network to access and retrieve patient, procedure and other information from the system database, located on a local server and/or optionally on an offsite redundant or backup server.

The invention may also be provided with stereoscopic and/or monoscopic microphones, located above the operative table and perimonitor to record procedure comments and notes and/or to receive voice commands for the system. Such voice commands might include "next page" or "emergency procedures" or "zoom in" or "zoom out" or "shift left/right/up/down." Additionally, the microphones may be provided for recording an audible "Timeout," commanding the system to suspend operations until a "time-in" or similar activation command. A "Timeout" team can be employed to enhance patient safety, encouraging a pre-procedural briefing clarifying the critically relevant information regarding the case, such as issues of identity, procedure to be performed, sidedness' concerns, etc. Additionally, this functionality enables transmission of other audible information as would be required when video conferencing, such as providing guidance to a pathologist regarding the pre-excisional orientation of a tissue sample sent for evaluation. Likewise, other stated data can be recorded as desired by the surgeon for subsequent review and/or hospital management to enhance quality control programs.

The present invention may also be provided with video cameras both above the operative table and peri-monitor to record procedures, conduct, and other visual information, as well as enable video-conferencing. This functionality provides a means for promptly addressing 'sidedness' deviations as soon as they occur via remote validation and observation as the procedure unfolds. The system accommodates cameras at any other location deemed necessary to record information or to make automatic adjustments to the overall system. Cameras also act as an interface device for inventory control when blended with a barcode, QR Code or other visual reference code.

According to the invention, speakers are provided, connected to the interface system to facilitate audio alarms initiated by predetermined limits within the system of the invention as well as those set by the surgeon to assist in time management during the procedure. Additionally, this function is necessary to allow video-conferencing during the case as would be required of intraoperative consultation as needed.

Computers & Processors—Various devices that manage the MFCD, redundant video displays, gesture-sensitive devices, video cameras and audio microphones are provided within the local unit itself. Other processors process data in real-time for storage as well as communicate through the built-in network to manage overall system health.

Wired & Wireless Human Interface Devices—Keyboard, mouse, trackball, optical scanner, gesture-sensitive camera, microphone, digital pad, joystick, fingerprint reader, smart-card reader, smart device; these devices enable custom solutions for various clients for any operating room configuration.

The software of the present invention includes programming which allows a standard computer monitor to function as the MFCD for the operating suite. This proprietary software, uniquely designed to meet the sterility needs of the surgical team while enhancing patient safety, enables the seamless integration of man and machine. The software may be configured to be accessed from any desktop/laptop/handheld device with means of securely interfacing with the data servers of the present invention. Under routine conditions, the doctor-patient interactions after an office consult occurs via secure protocols with a secure web site. The software may also be configured to cause data transfers to occur at a preset time to transfer data between a specific operating unit (local unit) and a central server on the management and data storage network, discussed herein below. When the operative procedure is complete, the data is stored in the specific operating unit until an appropriate time when the captured surgical data is pushed back to the central server. The operating theatre unit of the invention operates autonomously in a terminal-based mode once data is received. The management server manages all pre-operative and post-operative data processing. All checklist pages permit the addition of surgeon preferences, Surgeon Enhanced Standard of Care (SESoC) enhancing the Minimally Required Standard of Care (MRSoC), and descriptive/directive notes as deemed necessary to facilitate the best surgical outcome.

The software of the present invention generates and/or supports a number of interactive pages for display on one or more of the various display units of the invention. The categories of pages displayed include: 1) pre-procedural pages; 2) procedure preparation pages; 3) intra-procedural pages; 4) post-procedural pages; 5) recovery page; 6) patent feedback page.

1) The Pre-Operative/Pre-Procedural Pages may include the following pages:
  a) Administrative Page—This page records pertinent general patient information in compliance with the Joint Commission on Accreditation of Healthcare Organizations (JCAHO) and in accordance with Health Insurance Portability and Accountability Act (HIPAA) legislation.
  b) Demographic Page—This page records demographic information to provide for patient tracking purposes.
  c) Patient Information Page—This page records pre-operative information pertinent to the planned procedure, either elective or emergent. Multiple submenus include history & physical (H&P), review-of-systems (ROS), vitals, etc. Most importantly, critical information is initiated at this level including 'sidedness certainty' and known allergic reactions (medication, latex, etc.). In cases where 'sidedness' is crucial to successful outcome, an appropriate symbol (L or R with respect to prone or supine position) will be established as a permanent 'watermark' to be seen on every page subsequently associated with the case; the first of many checks to mitigate a devastating sidedness' mishap.
  d) Studies Page—This page records pre-procedural studies to be referenced during the case.
  e) Medication Insight Page—This page functionally addresses the frequently injurious medication dosing concern. Upon entering patient-specific data such as medication allergies and patient weight, the proper amount for each anticipated medication is pre-calculated to assist with dosage determination. Additionally, nutritional supplements and prescribed medications taken for chronic comorbidities are entered to highlight potential adverse cross-reactivity issues as well as possible side-effect profiles.
  f) Consent Page—This page records the surgical consent process as required by law and confirmed via Human Interface Device, ensuring both patient and healthcare provider acknowledgment. Where available with secure on-line access to the system of the invention, the prospective patient will have access to self-paced Educational Modules providing the patient with the necessary information as required to ensure informed consent.
  g) Handouts/Information Page—Patient handouts addressing preparatory instructions, recovery literature, risk of procedure information, medication information, etc. Access to the Patient Accountability/Patient Feedback Page is granted to allow the patient self-advocacy regarding the case.

2) The Procedure Preparation Pages may include the following pages:
  a) Validation & Profile Page—This page requires the surgeon to securely enter their personal and professional information to access the system, which then confirms valid credentials and privileges as required by law. This 'gate-keeper' function protects against individuals who do not have the necessary authority to proceed, preventing gross abuses associated with false credentialing and alleviating the harmful consequences of such dishonesty and misrepresentation. Secondly, this function is used to inform the provider of matters relevant to system status and functionality as well as training requirements necessary to maintain currency of the system.
  b) Operative Risk Mitigation (ORM) Page—This page collects data on each team member, via a brief questionnaire, to enable a unique real-time risk analysis indication to be displayed during the case. As team fatigue increases during the procedure, the color-coded ORM border indication, visible on every Intra-Operative/Intra-Procedural page, progresses on an analog scale from minimal risk (shades of green), to moderate risk (shades of yellow) to severe risk (shades of red). Each hospital can manage variables to determine what objective measures equate to each stage of perceived risk.

c) Surgeon Quick-Check Page—This page facilitates last minute pre-operative checks before the patient is transported from holding to the OR. Items tended on this page include accompanying family member contact information, procedural follow-up information, etc. Additionally, this page serves as another validation when 'sidedness' is a concern, confirming the surgeon has 'signed' the correct side of the patient as this is a commonly utilized technique.

d) Anesthesiologist Quick-Check Page—This page facilitates last minute pre-operative checks before the patient is transported from holding to the OR. Additionally, this page serves as yet another validation step to ensure confirmation of the correct 'sidedness' where appropriate and validation of the appropriate surgeon signature placement.

e) Surgeon Room Preparation Page—This page displays a pre-determined set-up checklist for required and preferred techniques and procedures as desired by the surgeon.

f) Anesthesia Room Preparation Page—This page displays a pre-determined checklist with requisite access to the preoperative data as needed, especially the Medication Insight Page to assist in all dosing calculations. The system connects to various pharmacy providers to show prescription history.

g) Scrub-Technician Room Preparation Page—This page displays a pre-determined checklist for required and preferred techniques as defined by the surgeon with particular emphasis on the scrub-technician's preferences to accomplishing the scheduled tasks. This page also manages room inventory.

h) Contact Page—A quick reference list including contact and pager numbers for individuals who may be required for consultation during the case (colleagues, equipment representatives, Code Blue Emergency, etc.)

i) Technical Support Contact Page—A quick reference to both telephony and video conference technical support professionals.

j) Other pages required for system administration.

3) The Intra-Operative/Intra-Procedural Pages may include the following pages:

a) "Time-Out" Page—Some current medical procedures include a "Time-Out" phase according to which a member of the surgical team, often the chief nurse, asks everyone to pause their activities and listen to a brief pre-procedural briefing during which patient and procedure details are outlined. Sometimes, however, while the procedure is "technically followed" where a member of the medical team calls "time-out," calls for everyone's attention, and then reads the briefing materials allowed, very few persons in the room actually stop to listen. The "Time-Out Page according to the invention permits recorded audio and visual confirmation that the "Time-Out" process has been accomplished by recording the operating theatre with a single wide-angle video camera shot, encouraging all surgical team members to remain attentive during this simple yet critical safety technique. When recording, the MFCD will display a flashing "Time-Out" banner.

b) Surgical Interface Page—The primary display on this page is the sequentially ordered interactive checklist, characterized by the Minimally Required Standard of Care (MRSoC) and the subordinate Surgeon Enhanced Standard of Care (SESoC) checklist steps. Data for the checklists will be acquired and loaded into the database from appropriate authorities where relevant. Where there is no current database, as is the case with the majority of operative procedures, they will have to be derived de novo. The proposed technique is to solicit the recommended Standard of Care (SoC) from recognized surgeons in their specialty throughout the United States. These individuals will be required to provide proper credentialing, board certification and licensing (where relevant). Additionally, other considered factors include procedural currency, the number of procedures performed and confirmation of good-standing among their peers and relevant academies. Lastly, litigation concerns must be addressed where appropriate. The most comprehensive sequence will be reviewed and edited by a peer of the same caliber, and—if approved—deemed the MRSoC for that specified procedure. The agreement will allow for changes to be implemented as the scientific community and generally accepted standards-of-care dictate, ensuring the most current techniques and procedures are incorporated into the MRSoC.

Figure 4:
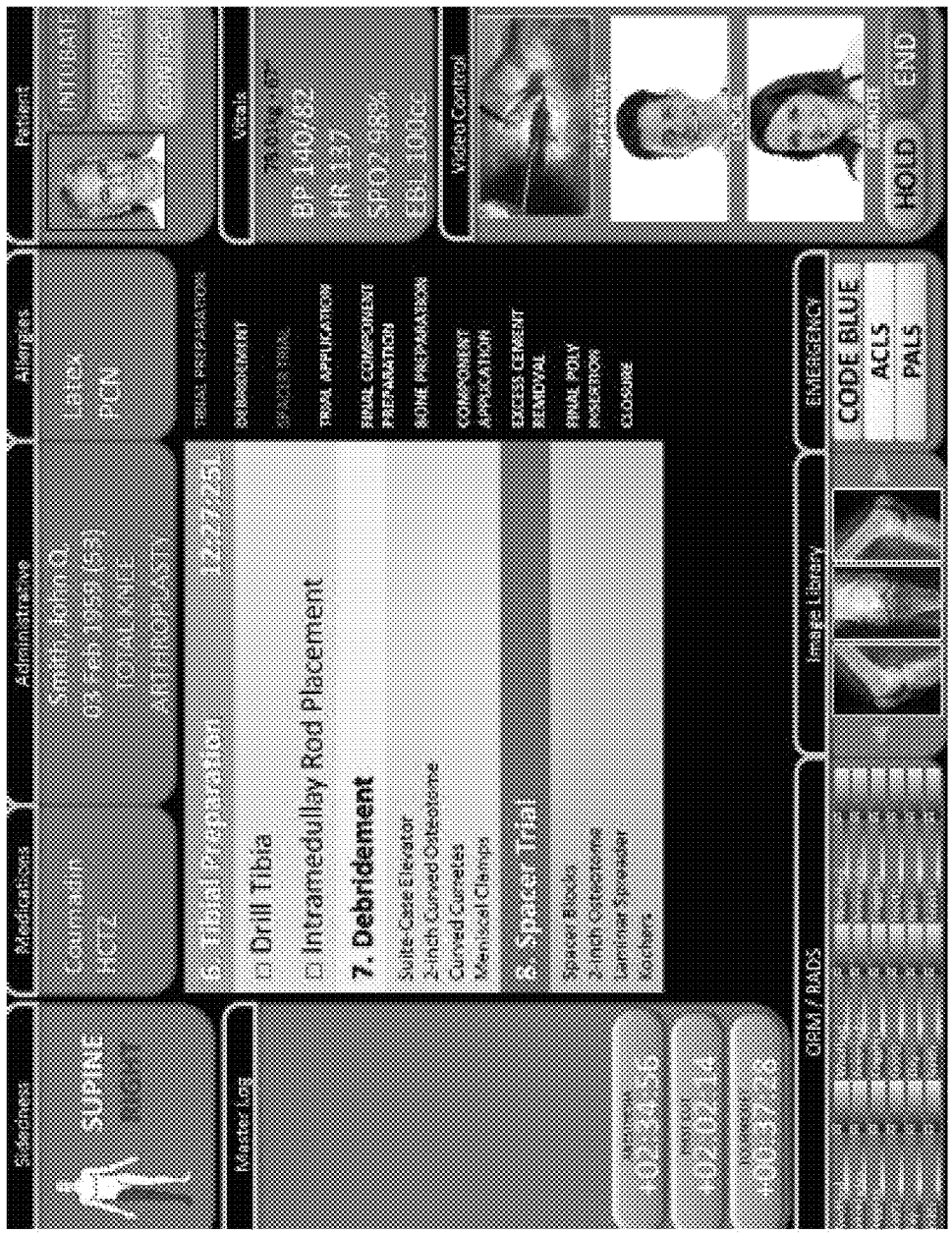
FIG. 4 is a screen shot from the primary display device during the intra-procedure mode of the invention according to an embodiment of the invention.

The Surgical Interface Page, an example of which is shown at FIG. 4, provides the highest fidelity to the operative process. It is the primary default display or 'homepage' of the system and easily referenced in the OR by all members of the surgical team; on primary and repeater screens. System alerts are managed on this page and are both visual and audible so as to demand the surgical team's attention, requiring active acknowledgement to silence the alarm in the spirit of primum non nocerum. In addition to the ORM border previously described, there are several links to access additional functions as needed throughout the procedure. A general description of this principle page is as follows:

i) The Surgical Interface Page displays the following information:
  (1) Date/Time
  (2) Patient Identification Information
  (3) Procedure Title
  (4) Surgical Team Member Names
  (5) Left/Right Sidedness' Watermark Symbology ii) The Surgical Interface Page contains access to directive "Emergency Procedure" tabs. Rather than rely on memory during such stressful emergencies, the required procedural management tree will be provided to the surgical team, assisting the team during resuscitation efforts. The protocols are presented in similar function and fashion as the primary checklist to provide support during such emergencies, including automated code blue alarms. Included are the following functions:
  (1) Advanced Cardiac Life Support (ACLS)
  (2) Basic Life Support (BLS)
  (3) Pediatric Advanced Life Support (PALS)

iii) The Surgical Interface Page contains "Information Management" functions:
  (1) Imaging—Computed-Tomography (CT), Magnetic Resonance Imaging (MRI), Plain Film (X-Ray), etc., allowing intraoperative reference without the need for additional monitors or backlights.
  (2) Patient Demographic Data
  (3) Video-Conference/Tele-Conference Interface
  (4) Gesture-Sensitive Interface Screen—A small review screen identifying what the gesture sensitive camera is receiving, confirming the intended individual is commanding the system.

iv) The Surgical Interface Page displays "Realtime Running" functions:
  (1) Running "Chat" Log—Records elective entries as desired by the members of the surgical team, to include the classical anesthesia log (fluids, colloids, blood products, blood loss, etc.) in addition to compulsory annotations which the system automatically inserts into the log as checklist steps are initiated and completed. All entries and system actions are time/date stamped.
  (2) Realtime Clocks—A case duration clock will initiate upon the acknowledgment of "the first cut." Additional clocks, such as a tourniquet duration clock, will also populate as required to enhance procedural safety. In the latter case, the timer function will launch when the "Apply Tourniquet Pressure" is initiated. After the preset MRSoC or SESoC defined time limit (whichever is shorter) has elapsed, a combined audio and visual alarm function alerts the team to transpired tourniquet time. After acknowledgment by silencing the audible alarm, the tourniquet pressure must then be manually released to allow tissue reperfusion, acknowledging the causal alarm, thus resetting the "Master" alarm.
  (3) Dosimeter—Records the amount of acute and cumulative radiation exposure to both the patient and the medical team throughout the case. This feature is intended to make sure that all personnel stay below OSHA exposure standards. The dosimeter results are recorded and stored in a central server and are available for display/reporting to each personnel when they logon to the system. The records are also available to administrative personnel. The cumulative amounts are updated after each individual procedure/instance of exposure.

v) The Surgical Interface Page displays the "Interactive" functions:
  (1) Interactive Checklist (IC)—This is a well-validated, interactive checklist directing the specific procedure to be performed, enhancing patient safety via increased procedural accuracy and efficiency while mitigating anticipated operative risk. In general, the IC displayed on the MFCD is customized to each procedure, enhancing team communication and active participation, outlining ideal technique and sequence as indicated by modern evidence-based medicine and provider preferences. The purpose of this function is to streamline often complex surgical processes, which are nearly always relegated to the mere memory of the attending surgeon. The IC displays the current step being performed and provides an anticipatory view of the subsequent steps as appropriate to the surgeon's preferences, reducing time lost to supply acquisition and equipment preparation and maximizing the efficiency of every member of the team. Retrieved from a central server and consisting of the MRSoC as agreed upon by the appropriate professional authority, the MRSoC will not be alterable by the healthcare provider. This safe-guard can only be modified by the controlling agent responsible for quality assurance and data fidelity. However, a SESoC allowance permits the surgeon to modify non-critical details of the case (procedural sequence, kit manufacturer, etc.) to their personal preference. This maximizes the professional latitude of preferred techniques while ensuring the MRSoC is preserved to safeguard patient safety and mitigate preventable injury. SESoC changes are retained for the next case and can be adjusted as necessary. Completion of each step requires acknowledgement via the sterile gesture-sensitive camera interface or the non-sterile human interface device before the next step is proffered. Most importantly, this visual checklist empowers every member of the surgical team, regardless of experience level or hierarchical status, to speak with relative authority when a suspected deviation from the expected procedure is perceived. This is the true realization of CRM migration from the aviation arena to healthcare, now known as provider resource management ("PRM"), the medical equivalent of CRM, allowing every team member the means to take ownership of the case and effect a positive outcome. The requisite SoC steps which form the IC are listed as alpha-numeric 'bullets,' starting with the initial "Call for Patient" and ending with "Transport Patient from Surgical Suite to Post-Operative Care." The MRSoC steps are of a clear font with appropriate size for monitor size and correct contrast for easy reading. The surgeon's variable SESoC steps are listed under the primarily associated MRSoC step to be processed as a customized alpha-numeric 'bullet.' In these cases where the surgeon has elaborated such steps, the primary 'bullet' will not permit an "accomplished" indication (checked-box) until all additional customized preferences are completed. Additionally, many procedures allow for sequential modifications, a variable decision tree, as desired by the surgeon while the case is in progress due to body habitus, co-morbid risk, etc. In these cases, such items will be identified in the MRSoC and the presenting page will indicate "either/or" steps to permit the surgeon to change the sequence flow as required (such as a preference to prepare the tibia before the femur in a total knee replacement). In either situation, after the surgeon selects the preferred decision tree and then completes the requisite steps unique to that tree, the program returns to the remaining MRSoC tree to ensure that all steps are accomplished. This function is only available where sequential deviation is not detrimental to the patient's care per the generally accepted SoC.
  (2) Realtime Imaging Page—Allows display and review of intraprocedural imaging such as scope and C-Arm image capture without the need of additional monitors.

vi) Alarm Function—While any page will display a visual "Master" alarm, accompanied by an audio alarm when necessary, the Surgical Interface Page serves as the alarm acknowledgment interface. An alarm function consisting of a Master Alarm indication as well as the associated causal alarm is displayed on the monitor. A flashing Master Alarm is triggered when an associated causal alarm is tripped. The flashing visual and associated audible tone warning requires acknowledgement, which consists of silencing the tone, resolving the discrepancy and then resetting the visual alarm. Thereafter the alarm is prepared for reinitiation as needed. Although the primary issue needs to be resolved before the visual alarm ceases, the audio alarm may be silenced prior to causal resolution to prevent nuisance alarm distraction.

vii) Accounting and Consumables Page—This functionality provides a means to account for intraprocedural expenditures such as the number of needles, sponges, etc. Additionally, this page maintains a running inventory replenishment function.

4) The Post-Operative/Post-Procedural Page records data in the traditional post-operative format as required per the surgeon's preference, hospital directives and those mandates required for complete accountability and billing. This page also captures audio and video instructions the surgeon may prescribe for the patient. A speech-to-text feature allows for real-time visual feedback that the surgeon's instructions are transcribed correctly.

5) The Recovery Page allows for complete recovery progression annotation. This is to be utilized in the post-operative phase as well as any requisite hospital stay prior to discharge.

6) The Patient Accountability/Patient Feedback Page provides the patient with the opportunity to be their own advocate and to take ownership of their healthcare. Carefully designed to comply with HIPAA requirements, this function is accessed by the patient at a time and place of their choosing; outside of the hospital and sometime after the surgery. In plain language, the patient is asked to complete a survey as preferentially designed by all interested parties (surgeon, hospital, insurance, etc.). The questionnaire could address common post-procedural complications and screen for such adverse sequela by phrasing key concepts in layman terms, such as "calf pain" rather than the synonymous medical term "claudication." This function provides a means to educate patients concerning indications and directs them to seek further medical attention where necessary. Additionally, this function serves as an adjunct reminder to schedule required follow-up appointments.

Instruction and training is critical to the effective and efficient implementation of the system of the invention. An important aspect of this successful healthcare transformation requires an honest self-assessment of the problematic hierarchical culture which has characterized western medicine since its inception. Currently, the operative culture is only as inviting as the personality of the surgeon performing the procedure. In such cases, the surgeon becomes the single point-of-failure, relegating the rest of the surgical team to ancillary fixtures to be heard only when addressed. Tragically, in instances where the surgeon is perceived as aggressive and non-inviting to suggestion, it is the patient who suffers. The time has come for each healthcare member to recognize their individual responsibility for a safe and successful procedural outcome; and that depends on the degree to which each member is convinced that their honest and inclusive participation is sincerely welcomed. To facilitate such dialogue, the working culture must remain free from fear of retribution or ridicule regardless of station or status. Medical procedural safety is ripe for revolution with the implementation of the present invention.

The requisite training consists of three distinct elements:
1) Initial Qualification Training—The basic interface procedures required to effectively interact with the system of the invention via the associated software and hardware will require one-time orientation. Additionally, a portion of the initial training will require introductory instruction emphasizing the principles of leadership, assertiveness, decision making and professionally courteous communication, with primary focus on the goal of enhancing patient safety.
2) Recurrent Training—All healthcare providers will be required to attend refresher training to review and update the most current system methodology as major software updates are available. Given an appropriate non-attribution policy (a policy that renders anonymous any disclosures of actual or potential mishaps that do not result in patient injury), coursework would vary with emphasis on particularly recent 'lessons-learned' in hopes of reducing subsequent occurrences, similar to current Morbidity and Mortality ("M&M") residency requirements. Specific human factor analysis would include critical incident analysis and identifying "near-miss" incidents. When appropriately presented devoid of identification, illustrative audio and visual samples from hospitals using the system of the invention would be used to the benefit of all in network; reaching beyond the walls of a single hospital. In the landmark Institute of Medicine study entitled To Err is Human, one of the recommendations to improving patient safety is designing a means for a healthcare provider to self-report an actual or potential medical mishap (frequently referred to as a "near miss." The system of the invention will allow a self-reporting function if any such incident of medical significance should occur. Reports will be preferably rendered unidentifiable after 24 hours (with the exception of medical negligence), and could provide 'lessons-learned' material if suitable for annual refresher training and/or M&M as applicable. Additionally, on a regional or national scale, such data could provide the earliest indications of worrisome trends that would have otherwise gone unnoticed
3) Simulation Lab—There is no substitute for the real thing, but modern simulation labs for the medical professions provide extremely realistic training with high fidelity; an excellent adjunct to didactics. Training will require initial and recurrent Simulation Labs to practice and perfect the concepts presented in class.

The following section will describe functional relationships and requirements of the invention, chronologically from the time when a physician joins the network to develop their own unique surgical methods through final patient feedback after their procedure. According to the invention, each medical procedure is established in the system as a "tracked" item cycle, which begins with patient assignment and concludes with post procedural patient feedback.

Physician registration, authentication and authorization occur as a one-time event, while the physicians' checklist customization is recurrent.

Requirements and Interactions

Figure 2:
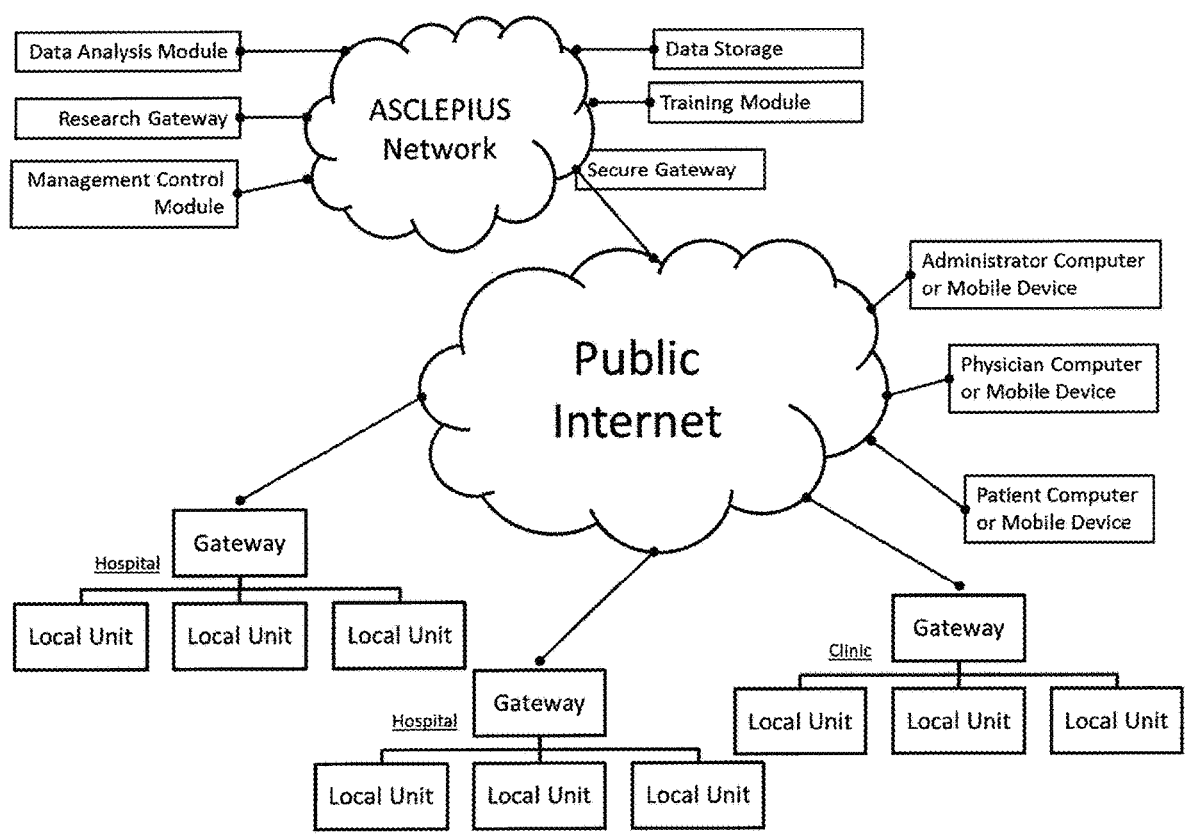
FIG. 2 is a schematic showing various elements according to an embodiment of the invention and potential connections between them.
Figure 3:
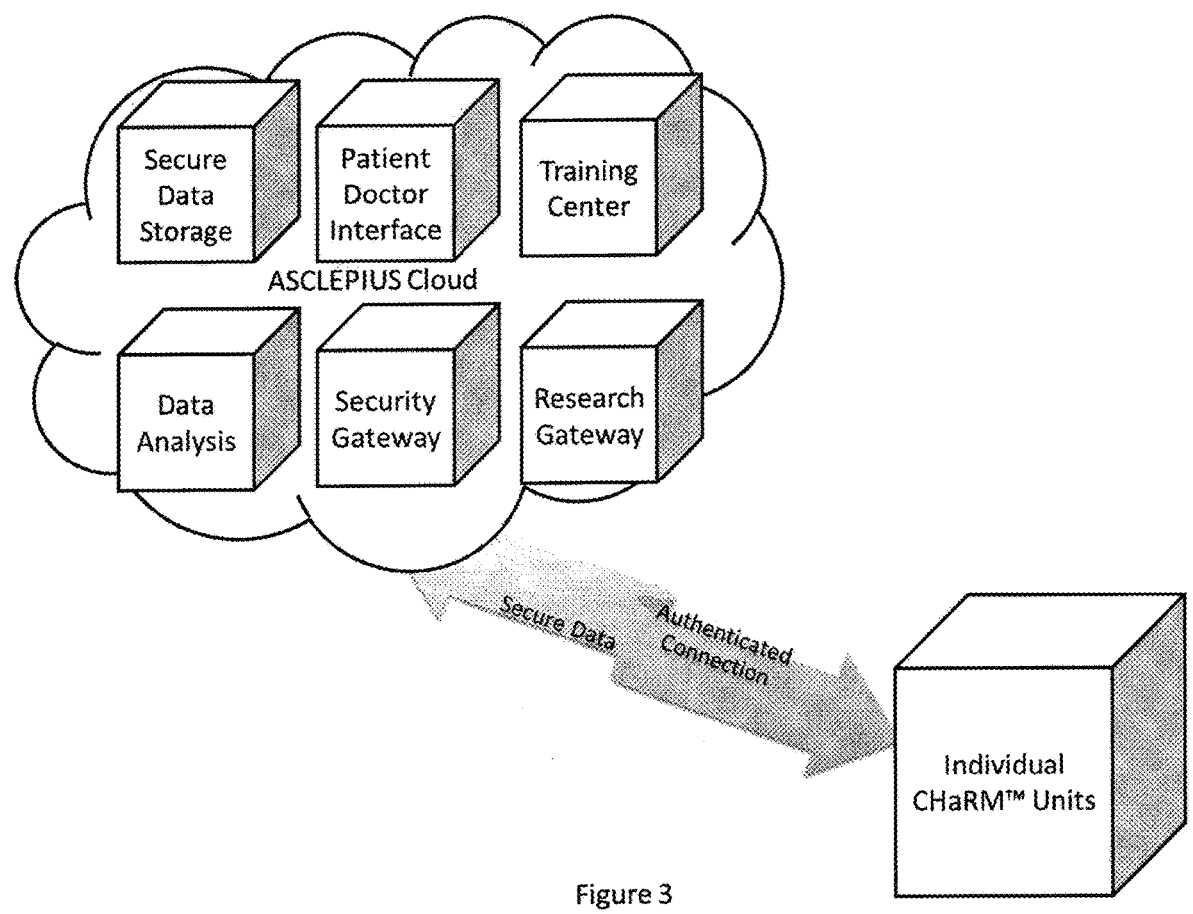
FIG. 3 is a representation of certain elements of the data and control network of the invention and its interaction with local units of the invention.

A customer service representative grants access to the approved physician on the Health Insurance Portability and Privacy Act (HIPAA) capable server, see, e.g., "data storage" on the Asclepius Network and "Secure Data Storage" on the Asclepius Cloud, FIGS. 2 and 3, respectively. The physician has access to a standardized library of pre-approved checklists that they can modify to fit their own styles and expertise. Checklist customization can be to rearrange, add, delete, expand upon or otherwise change checklist steps within certain rules and parameters as determined by the Parallax Enterprises reviewing team. When a physician saves a customized checklist, it becomes open source among system subscribers, available in a user-defined library on a system server where another user can copy/modify the checklist. In the end, a single user will always have access to their original checklist regardless if it has been copied/modified by another user. Also, any checklist will be "offline" until it is approved by a reviewing team member according to what is defined as the Minimally Required Standard of Care (MRSoC) following evidenced based-medicine practices. Once approved "online", the checklist can be further modified for each patient, encompassing patient-specific needs or restrictions in what is defined as the Surgeon Enhanced Standard of Care (SESoC).

The physician assigns the surgical procedure checklist to a specific patient and assigns a surgical date. The patient accesses the HIPAA capable server (hereinafter "HIPAA server") and is briefly assessed to determine their 'medical literacy' level. The patient completes appropriate online questionnaires and receives a Computer-Based Tutorial (CBT) (distributed through Adobe Flash browser plug-in) about their upcoming surgery. The system contacts the patient by automated telephone/email at predetermined times prior to the surgery to ensure there are no changes to the patient's health that would adversely impact the procedure as well as remind them of the their pre-surgical obligations, such as when to stop eating or drinking the evening prior. The system also captures projected surgical dates to schedule each system resource (local units), ensuring local unit availability for the entire procedure. This requirement can be found in the Non-Functional Specification Document in determining scheduled or periodic maintenance.

On the day of surgery, the scrub technician interacts with the local Operating Room unit to download that day's surgeries, which may include multiple procedures from various physicians or various procedures for the same surgeon. The HIPAA server packages data in a predetermined format (XML-parsed) and passes that information to the local unit via Transport Layer Security (TLS) secure protocol. The local unit unpacks and stores the data, then pre-processes the data in anticipation of the procedure. These steps are standard for each hospital and would be downloaded with each surgical procedure with customization according to the preferences of each surgeon. Setup steps are open-ended and may change regularly. The local unit records the completion of each step along with a date-time stamp and other pertinent data. In certain steps, verbal or visual responses are required and the local unit records the critical audio or video for later processing and retrieval.

The local unit constantly "listens" for key phrases while procedurally active. The key pneumonic is "CHARM" followed by a slight pause and the system will be ready to accept a wider range of verbal commands. This minimizes random and unintended automated actions by the system. These commands are for specific crisis action items, such as a "Code Blue" cardiac arrest, prompting the system to display, initiate and record certain events.

Following each surgical procedure, the system, preferably via the local unit, interacts with the physician in a predetermined checklist unique to each physician and unique to the procedure to facilitate follow-up. Additionally, it serves as a crucial inventory asset to account for surgical devices and materials such as sponges, needles, etc. The physician would determine what items would be used for follow-up during the initial assignment phase and the checklist would be downloaded during subsequent local unit setup. The system would capture text data, such as typed instructions as well as any audio or video the physician determines pertinent.

After the physician loads all post-operative instructions and orders into the local unit, the system packages audio, video and data for simplicity of transfer. The local unit can then be initialized for a subsequent operation or placed in a standby mode. At a predetermined time based on network traffic or system workload, the local unit connects to the remote HIPAA server to return the post-operative package to the server for secure storage. Follow-on audio, video and data processing occurs to remove HIPAA-related information from certain data, while the patient-centric information is compiled for follow-on automated notifications to both the patient and physician as well as hospital staff tasked for process improvement.

At predetermined times, the system uses automated telephone, email and/or text message to send follow-up recommendations to the patient. This could be a directive to call 9-1-1, instructions to return to the emergency room if certain conditions exist, remind to take a short-term medication, or possibly perform certain mobility exercises to aid in patient recovery. Since the physician verbally annotated the directives, the system allows the doctor to "tell" the patient at those predetermined times.

In a more long-term follow-up process, the system allows each physician to see all patient follow-up tasks in a calendar through the web server. With some follow-up tasks exceeding 6 months, the system would continue to follow a patient by providing periodic reminders until the minimum period expires or the physician releases the patient from the procedure, whichever occurs last.

Terminology

The system management and data storage network of the invention, hereafter referred to as "Asclepius" (the God of Medicine and Healing in ancient Greek religion), the Asclepius network or the Asclepius cloud (see FIGS. 2 and 3), includes a collection of networked servers capable of web interaction as well as direct access to individual local units. Asclepius maintains the qualities commensurate with HIPAA protection, in that all data stored is both physically and electronically protected through multiple layers of authentication and authorization, transmitted through secure protocols, and physical access restrictions and accountability exist at the server station. Also, the system maintains an electronic log of access granted with data sent. The physical computer site maintains physical/restricted access and provides terminal access logs on demand. A second geographically-separated site mirrors the first and acts as a failsafe for a catastrophic event.

Individual local units sit in each operating room, emergency room, doctor's office or some other medical, dental or veterinary clinic. They are stand-alone systems connected through standard network and power cables. They require no on-site privileges from the host hospital except for internet access and standard outlet power. Local units preferably run Microsoft Windows operating system, which provides improved connectivity to the certain gesture-sensitive cameras and microphones.

Functional steps fall into one of eight phases: Initiation, Transfer-in, Pre-Operative, Operative, Crisis Action, Post-Operative, Transfer-out, and Follow-up. Initiation includes checklist customization and assignment to the patent as well as patient interaction with the system. Transfer-in begins with the electronic packaging of the surgical data along with certain prepositioned checklist items, through data acknowledgment and verification with the individual local unit and ends after pre-processing within the local unit. Pre-Operative phase begins when the specific surgical procedure is queued as active and includes all functions, tools, supplies, interactions and data management until the physician is ready to begin the actual procedure. The Operative phase and Crisis Action phases can run concurrently and include checklist management, data recording, and video and audio recording (but not necessarily processing). The Crisis Action phase includes specific emergency checklists and associated data capture that identifies it as such. Post-Operative begins when the operative checklist is closed and includes physician-directed instructions and orders associated with certain close-out requirements. At the end of Post-Operative, the Transfer-out begins with data packaging and storage until a time when the package can be securely transferred to Asclepius. This phase may be interrupted by a subsequent procedure, resulting in numerous procedure data packages queued for Transfer-out at an appropriate time. Transfer-out ends after Asclepius acknowledges receipt of a verified transfer package. Follow-up includes all actions with Asclepius including automated patient reminders, a combined physician follow-up calendar, follow-up surgical notes (not necessarily patient related), and patient feedback.

Physician checklists provide a general guide as to how each physician will conduct a procedure based upon generally accepted standards, as defined by the MRSoC and the SESoC, as well as the specific needs of the patient. All checklists, regardless of type, include a source annotation, publication date, review date and specific contact information for the originator. Also, all checklists forever reside in the system, but only those tagged as "published" are available for use by other users. Asclepius manages the accepted core checklists for each procedure, from which physicians can copy and modify based on their own preferences, knowledge and experience. These modified checklists reside in a global directory along with, but annotated separately from, the core checklists. Physicians can manipulate and publish as many checklists as they desire, but all checklists must pass a legal and medical review before the system allows the checklist to be used. When the physician assigns a new checklist to a specific patient procedure, the modified checklist becomes a customized checklist, such as would be the case of unique qualifiers like a latex allergy, and can only be used for that specific patient procedure.

There are several critical components that directly impact the basic functionality. Those listed here are not all-inclusive, but are required to ensure compliance and capability. Other ancillary functions that enhance system ease-of-use or administration can be found in the Non-functional Specification Document.

Users

There are four main categories of users: patients, physicians, facilitators and administrators. Patients cannot self-register and must be provided specific login credentials for their procedure. Once the physician processes the final post-operative feedback and closes the cycle, the patient's login credentials expire permanently for that procedure. There are no sub-groups of patients and no patients have visibility on any users other than their physician.

The physician group can self-register but approval to gain access though the system is provided after an administrative review. This group has access to a larger online library of training, online courses, checklists, announcements and other future information channels. Physicians have visibility on all their patients and may be granted periodic visibility on other physician's patients. Physicians have a tiered hierarchy of visibility; for instance, a chief of surgery at a hospital would have visibility (but not control) over patients of physicians who work under them.

Facilitators include individuals who have authority to move data to and from Asclepius. Facilitators have a very limited role but will have access to patient data and therefore would only be granted access from IP address and using MAC addresses commensurate with systems they should use.

The administrator group contains several layers of access and control, and includes such roles as technical support, medical/HIPAA support (when patient data will be accessed), other non-functional levels described in a separate document. Administrators, in general, have visibility and control over all users and data.

Administration

Administration controls should be available at every level of the system from Asclepius to each local unit. Administrator access is tightly controlled with all functions logged for specific review to comply with HIPAA regulations.

Error Handling

All error handling should be user-friendly. For example, web-based physician or patient input should be reported to the user until a valid solution is reached.

Individual local units log errors and faults for upload to Asclepius during the Transfer-Out phase. Local units also categorize errors based on severity (nuisance, moderate, critical, failure) in both software and hardware components. Local units will incorporate redundant software and hardware backup strategies based on system engineering and failure analysis during the design phase.

Regardless of the errors, the system should make specific record of all errors per the ISO9000 strategy.

Security

Patient data security is paramount. The security strategy is consistent across all users, all groups and all systems: simple is not good enough. Network and physical security will exist at Asclepius through a HIPAA-certified provider, where both electronic and physical access logs provide the ability to data-mine for unauthorized access attempts as well as unauthorized releases of HIPAA information or the injection of malicious code. HIPAA information transferred from Asclepius will be through industry standard Transport Layer Security/Secure Sockets Layer protocols and IP address restrictions (a patient in Maryland should not have a foreign IP address, while a patient in England should not have a South American IP address). Asclepius will only release system data to known MAC addresses and IP addresses of the specific local unit. All access to and from Asclepius is logged by date/timestamp, IP address, MAC address, username, and login failed Boolean (if applicable), as well as other non-critical information such as operating system, web browser and referrer.

Patients use a predetermined, random username and password combination along with a patient-generated personal identification number.

Physicians at all levels will use a 2-part password authentication where a username and password combination is authenticated and the physician would enter a follow-on password based on a photograph they initialized during their training. Because the physician expects the photograph in the 2-part authentication, any spoofed website attempting to collect data would not have access to, nor present, that image. Also, this enhances the server authentication through the use of a second password.

Facilitators will use a 2-part authentication for the system. The username and password will be specific to each facilitator but the second part of the 2-part authentication will be with a secure access key which provides an incremental, date/timestamp, unique identification to Asclepius, which in turn validates the access key with the key server(s). This validates that the physical key is in the system after an authorized user has requested access to the system. Asclepius will not authenticate a facilitator without this physical key in the system and the system requesting from a predetermined IP address with a known MAC address.

Administrators at all levels will preferably use secure access keys for 2-part authentication regardless of whether HIPAA information is involved.

All passwords will be changed every 90 days. Password retrieval for physicians, facilitators and administrators will be through a valid email link with an on-file, verified address; else a customer service representative will need to be involved to use information gathered at initial physician training.

Physical security exists at all levels. Software security will be reviewed from the design phase to implementation by an independent security specialist in both Asclepius and local units. Software design will lock down unused universal serial bus (USB) ports to prevent certain vulnerabilities as well as configuration checks to prevent unauthorized hardware changes that could compromise security. Local units contain disks which hold HIPAA information and therefore would be controlled items in each hospital.

HIPAA

In addition to functional security measures mentioned, all access to HIPAA information will provide a standardized HIPAA notice along with a "consent to monitoring" banner after authentication but before any HIPAA information is displayed.

Technical Support

Technical support will be available at all levels within the functional architecture either through telephone or online live support. Technical support representatives will have the ability to manage any function for patients, physicians or facilitators, but not necessarily all administrators and certain administrative actions.

Technical support will divide into two areas: Asclepius and local units. Asclepius support will have authority and access to move data between Asclepius and local units. Unit support will only manage unit issues, but will have remote access to the equipment.

Smart handheld devices can wirelessly connect to an encrypted wireless signal from each local unit, allowing for a portable device (iPad, iPod or other smart, camera-equipped device) to act as a video teleconference platform. Even in the operating room, non-interference technical support is possible even in the middle of a surgical procedure. This, by definition, means that all technical support representatives will require internal HIPAA certification.

Printing and Reporting

At this time, there is no plan for immediate printing needs other than login instructions for patient access, post-operative procedural note to be included in the hospital record and an instruction sheet for the facilitator to transfer data to and from Asclepius.

Any printed material for patient consumption will be electronically recorded and compiled to the patient file. All printing will include a HIPAA statement along with "destroy when no longer needed" in the footer.

The system will include a PDF generator to allow for controlled printing or electronic storage of material.

Interfaces

Interfaces include web page access to Asclepius, screen access to the local units and smart handheld device access to local units. There is also a voice activated and hands-free gesture capability to interact with the local units.

Boundary Conditions

Asclepius will need to handle up to 10,000 users per day at the near-term maximum capacity. This is well within design specifications of most Linux-based web servers. Storage capacity should be scalable and capable of storage commensurate with the size of audio, video and data received from the local units.

Individual local units will be configured to manage at least 12 surgical procedures per day with a storage capacity to hold at least three days of post-operative information to allow for network connectivity issues.

Platforms

Local units will have two platforms: a Microsoft Windows operating system running on a blade server to interface with the gesture sensitive device drivers. A second blade server utilizes a Linux platform to capture data and perform pre-processing and it provides the communication between the local unit and Asclepius. The second blade server also utilizes a "localhost" web server to provide a future capability to a wireless smart handheld device. A commercial-grade router with wireless capability binds the system together.

All operating system configurations will eventually run through a virtualized machine, enhancing security, decreasing support requirements and increasing unit performance over a traditional operating system configuration.

Asclepius utilizes Linux with an Apache web server, MySQL (or similar) database, cPanel, and other industry standards for web hosting.

Local units will have a standardized operating system configuration that includes software (add-on and core system), as well as standardized hardware components. Also, all servers in the system will turn off unnecessary system services to free resources as well as a security measure.

Internationalism

The system will include a variable to customize any displays with another language. System administrators can set default languages, and each individual users can select languages for their interface at logon and/or at a preferences screen.

Portability

The local units are designed as portable in that they can be moved within an Operating Room to facilitate ideal viewing regardless of case set-up requirements. The facilitator will need to place the system in a non-network mode before disconnecting network cables. Also, standard outlet power supplies an Uninterruptable Power Supply (UPS); upon disconnecting the system from outlet power, the system will revert to battery-only during the relocation. The system will begin a timer that displays 50% of expected battery life as a notice to reconnect external power before the timer expires.

Local units are assumed to be assigned to a particular hospital, but if a unit is removed or replaced, the MAC address and IP address within Asclepius can be easily reconfigured.

Expandability

The system of the invention is expandable in both the hardware and software components. Individual units may utilize off-the-shelf technology in modular construction. Blade servers can be removed and upgraded with very little change to the physical structure.

Local units will include a wireless capability to remotely connect to smart handheld devices utilizing HTML5 standards as well as MAC address and IP address restrictions for security. Standard IEEE 802.11 protocols are supported by nearly every handheld device and routers allow for security measures to limit and allow connectivity. Utilizing the second blade to run a web host, more wireless handheld devices can expand capability without adding structural or power requirements to the system. Also, current technology allows for wireless camera and microphones to connect with the encrypted IEEE 802.11 router to capture even more data.

Asclepius is a hosted solution built upon scalable processors, disk space and utilities. The system dynamically grows and shrinks based on server load and requirements. Current tools exist to measure capacity over a period of time to determine excess capacity during peak loads to ensure a fully-capable system during those times of expected workloads.

What is claimed as new and desired to be protected by Letters Patent of the United States is:

1. A medical procedure and information enhancement system comprising:
    a colored display;
    a computing device having memory and processors;
    computer-readable media containing computer instructions for displaying a plurality of electronic pages;
    an interface through which a user may input information concerning procedures, preferences, observations, and outcomes, which information becomes available for display on one or more of said electronic pages;
    said electronic pages including a color-coded real time fatigue risk display for each team member during said procedure and a sequentially ordered interactive procedure checklist with visual and audible system alerts, said computing device configured to simultaneously display each step in the checklist as it is performed and each immediately subsequent step as a prior step is being performed, said computing device further configured to require and receive an authorized acknowledgement by a user via said input device that the current step has been completed before advancement of the display from a current step in the checklist to a next step in the checklist, and then advance to said next step in the checklist based on the received authorized acknowledgement.

2. A medical procedure and information enhancement system according to claim 1, further comprising one or more video cameras situated and configured to record a pre-procedural time-out briefing, wherein said electronic pages further comprise a timeout page displayed during said pre-procedural time-out briefing, said timeout page including audio and visual time out status indicators, patient name, procedure title, and sidedness indication, and wherein the system is configured to require use input via said interface to confirm that the time-out briefing has been completed prior to advancing said display to a procedure page.

* * * * *